United States Patent [19]

Gedeon et al.

[11] 4,421,113
[45] Dec. 20, 1983

[54] METHOD AND APPARATUS FOR CONTROLLING LUNG VENTILATORS

[75] Inventors: Andras Gedeon, Täby; Ulf Lundell, Grödinge; Göran Pilenvik, Stockholm, all of Sweden

[73] Assignee: Engström Medical Aktiebolag, Bromma, Sweden

[21] Appl. No.: 269,782

[22] Filed: Jun. 2, 1981

[30] Foreign Application Priority Data

Jun. 18, 1980 [SE] Sweden .............................. 8004530

[51] Int. Cl.³ ............................................ A61M 16/00
[52] U.S. Cl. ............................ 128/204.23; 128/204.18
[58] Field of Search ...................... 128/204.21, 204.22, 128/204.23

[56] References Cited

U.S. PATENT DOCUMENTS 3,923,056 12/1975 Bingmann ....................... 128/204.21
4,281,651 8/1981 Cox ................................. 128/204.23

Primary Examiner—Henry J. Recla
Attorney, Agent, or Firm—Browdy and Neimark

[57] ABSTRACT

For the purpose of carrying out an MMV-treatment (Mandatory Minute Volume) by means of a lung ventilator which includes a breathing-gas source from which a patient connected to the ventilator is able to breath spontaneously through an inspiratory line, and a ventilator unit which can be activated by means of a control signal so as to deliver to the patient through the inspiratory line a mandatory breath of determinable tidal volume from the breathing-gas source, the flow of breathing gas through the inspiratory line is continuously sensed by means of a flow meter. In a control unit there is generated a signal which is representative of the continuous integral of the difference between a reference signal and the flow signal from the flow meter. The value of the integrated difference signal is compared with a given limit value. Each time the value of the integrated difference signal reaches the limit value, the ventilator unit is activated to deliver to the patient a mandatory breath of given tidal volume. Alternatively, the ventilator unit may be arranged to deliver to the patient mandatory breaths of a constant given frequency and of a tidal volume, whose magnitude is determined with each mandatory breath, by the difference prevailing between the value of the integrated difference signal and the limit value.

9 Claims, 4 Drawing Figures

METHOD AND APPARATUS FOR CONTROLLING LUNG VENTILATORS

The present invention relates to a method and a corresponding apparatus for controlling a lung ventilator of the kind which includes a source of breathing gas, an inspiratory line having means for connecting the same to the airways of a patient and through which said patient can breathe spontaneously from said breathing-gas source; a ventilator unit which can be activated to deliver to the patient through said inspiratory line a mandatory breath of determinable tidal volume from said breathing-gas source; and an expiratory line which can be connected to the airways of the patient and through which the patient can exhale.

The most common method of treating a patient by means of a lung ventilator is the so-called CMV method, i.e. controlled mechanical ventilation, in which the patient is subjected to artificial breathing by the lung ventilator, the mandatory breaths applied to the patient being of a given frequency preset in the lung ventilator and each of the breaths comprising a given volume of gas, the so-called tidal volume, which is also preset in the ventilator. In this way, the patient is given by the ventilator a determined volume of breathing gas each minute, the so-called minute volume, which is the product of the frequency of mandatory breaths per minute and the tidal volume. In this method of treatment, the patient is unable to breathe spontaneously and is rendered a completely passive receiver of the ventilation determined by the lung ventilator.

In recent times the view has prevailed wherein, in many repsects, it is an advantage to allow the patient to attempt to breathe spontaneously from the breathing-gas source of the lung ventilator, and to support such spontaneous breathing with mandatory breaths applied by the ventilator to the extent that such are required to obtain satisfactory ventilation of the patient. In this way it is possible, among other things, to reduce the treatment time and the load on the circulatory system of the patient. The most advanced treatment method of this kind is the so-called SIMV-treatment process, i.e. synchronized intermittent mandatory ventilation, in which, principally, the lung ventilator forces upon the patient mandatory breaths having a tidal volume determined by the lung ventilator and of such low frequency, which is also determined by the ventilator, that the patient is able to breathe spontaneously between said mandatory breaths. By assessing the patient's own ability to breathe spontaneously and by adapting the frequency of the mandatory breaths applied to the patient in respect hereto, it is ensured that the patient obtains the desired total ventilation. One disadvantage with this method of treatment, however, is that the breathing pattern becomes very irregular with respect to frequency and uneven with respect to the size of the breaths. Furthermore, any rapid deterioration of the patient, where the patient suddenly ceases to breathe spontaneously or breathes spontaneously to a far less extent than had been anticipated, will result in dangerous sub-ventilation of the patient. If, on the other hand, the patient quickly improves, such that the paitent is able to breathe spontaneously to an extent sufficient to obtain fully satisfactory ventilation, he will, in spite of this, be subjected to mandatory breaths by the lung ventilator, which will disturb the fully satisfactory normal breathing of the patient, thereby to cause the patient discomfort and irritation. In order to avoid these undesirable and, with respect to sub-ventilation, dangerous situations, it is necessary to constantly supervise the patient; such supervision is not readily possible in practical clinical-care situations.

For the purpose of eliminating the disadvantages of the SIMV-treatment method, there was introduced in 1977 a treatment method designated MMV ("Mandatory Minute Volume"), which is described in Anaesthesia, 1977, Vol. 32, pages 163-169, "Mandatory Minute Volume. A new Concept in Weaning from Mechanical Ventilation", A. M. Hewlett, A. S. Platt and V. G. Terry. In this method of treatment the lung ventilator determines the total ventilation of the patient, i.e. the gas volume supplied to the patient per minute, i.e. the minute volume. Provided that the patient is able to spontaneously breathe this minute volume, he or she is not subjected to mandatory breathing by the lung ventilator. If, on the other hand, spontaneous breathing by the patient falls beneath the given minute volume, the lung ventilator applies mandatory breaths to the patient with a tidal volume determined by the ventilator, so that the patient obtains the whole of the pre-determined minute volume. Known apparatus with which such MMV-treatment methods are carried out comprise a ventilator unit and an expandable vessel to which breathing gas is continuously supplied in an amount corresponding to the desired total ventilation of the patient, i.e. the minute volume, and from which the patient can breathe spontaneously. If the patient is unable to breathe the whole of the amount of gas supplied spontaneously, the expandable vessel will eventually become filled to its maximum volume, whereafter surplus breathing gas which the patient is unable to inspire spontaneously is passed over to the ventilator unit and collected therein. When, in this way, there has been collected in the ventilator unit a volume of gas corresponding to the pre-determined tidal volume for a mandatory breath, a mandatory breath of said tidal volume is supplied to the patient by the ventilator unit. In this way, the patient is always supplied with the pre-determined minute volume of breathing gas, either by spontaneous breathing from the expandable vessel or in the form of mandatory breaths from the ventilator unit.

The known practical realization of the MMV-method is encumbered, however, with both practical and principle disadvantages. Thus, when breathing spontaneously the patient is unable to inspire more gas than the pre-set minute volume, since all of the gas contained in the vessel will be consumed thereby. This is a serious disadvantage, since usually the level of total ventilation is preset to a level slightly beneath the level of "normal" ventilation, so that the patient is, in this way, stimulated into attempting to breathe naturally. Thus, it is expected that the patient will be able to reach the set ventilation level, i.e. the set minute volume, and while doing so the patient will occasionally exceed this level. The volumetric capacity of the expandable vessel will, in this respect, determine whether, and for how long, the patient can obtain a greater minute volume than the set minute volume, by spontaneous breathing. If the volumetric capacity of the vessel is small, it will be rapidly emptied and the aforementioned time period will be very short. If a vessel of large volumetric capacity is used, the patient is able to inspire spontaneously a greater amount of gas than that corresponding to the set minute volume over a somewhat longer time period before the vessel is emptied. If, however, after the vessel has been completely emptied, the patient then suddenly ceases to breathe spontaneously, a correspondingly long time is required to fill the vessel to its maximal capacity and to pass enough gas to the ventilator unit so that a mandatory breath can be delivered to the patient. Thus, under these conditions, the patient must wait a relatively long time for the first mandatory breath, which can result in serious complications.

Known lung ventilator constructions for MMV-treatment have also two more fundamental disadvantages. One of these disadvantages is that the guaranteed ventilation of the patient is always the same as the pre-set minute volume of breathing gas supplied to the expandable vessel. Other more suitable physiological magnitudes, such as for example the alveolar ventilation, can not be utilized for setting or varying the applied minute volume. The other disadvantage is related to an objection sometimes raised to the use of the MMV-treatment method, namely that a patient may pant, i.e. take very shallow breaths at high frequency. In such a case the patient may receive by spontaneous breathing a total amount of gas which appears satisfactory, i.e. reaches the pre-set minute volume, without the patient actually being able to absorb a sufficient amount of oxygen and to get rid of his or her carbon dioxide, i.e. to obtain a really satisfactory ventilation. These problems can not be eliminated with the known lung ventilator constructions for MMV-treatment.

Consequently, an object of the present invention is to provide a novel method and a corresponding apparatus for controlling a lung ventilator for carrying out MMV-treatment method, which are not encumbered with the aforementioned disadvantages.

With this object the invention provides a method of controlling a lung ventilator comprising a source of breathing gas, an inspiratory line having means for connecting the source to the airways of a patient and through which the patient can breathe spontaneously from said breathing-gas source, a ventilator unit which can be activated to deliver a mandatory breath of determinable tidal volume from said breathing gas source, and an expiratory line which can be connected to the airways of the patient and through which the patient can exhale; the method being characterized in that the flow of breathing gas through the inspiratory line or the expiratory line is continuously sensed and a signal representative of the momentary value of said flow is generated; that a signal is generated which is proportional to the continuous integral of the difference between a reference signal and said flow signal with consideration being taken to the sign of the signal difference; that the value of the integrated difference signal is compared with a first given limit value; and that the ventilator unit is activated to deliver a mandatory breath to the patient in dependence on the result of said comparison.

In a preferred embodiment of the invention the ventilator unit is activated to deliver a mandatory breath of given tidal volume to the patient each time the value of the integrated difference signal reaches said first limit value.

The invention provides also a corresponding arrangement for controlling a lung ventilator of the kind mentioned in the foregoing, which arrangement is characterized in that it comprises a flow meter for continuously sensing the flow of breathing gas through the inspiratory line or the expiratory line and generating a signal representative of the momentary value of said flow; means arranged to generate a signal representative of the continuous integral of the difference between a reference signal and said flow signal; and means arranged to compare the value of the integrated difference signal with a first limit value and to generate said control signal for the ventilator unit in dependence on said comparison.

The invention is not limited to any specific structural design of the actual lung ventilator, but can be applied with any type of lung ventilator which permits spontaneous breathing of the patient and which comprises an electrically controllable ventilator unit which can be activated in response to an electric control signal to deliver a mandatory breath of desired tidal volume to the patient, and in which it is possible to continuously measure the magnitude of the flow of breathing gas being received by said patient.

The invention will now be described in more detail with reference to the accompanying drawing, in which FIG. 1 illustrates by way of example a simplified block diagram of a lung ventilator constructed in accordance with the invention;

Figure 1:
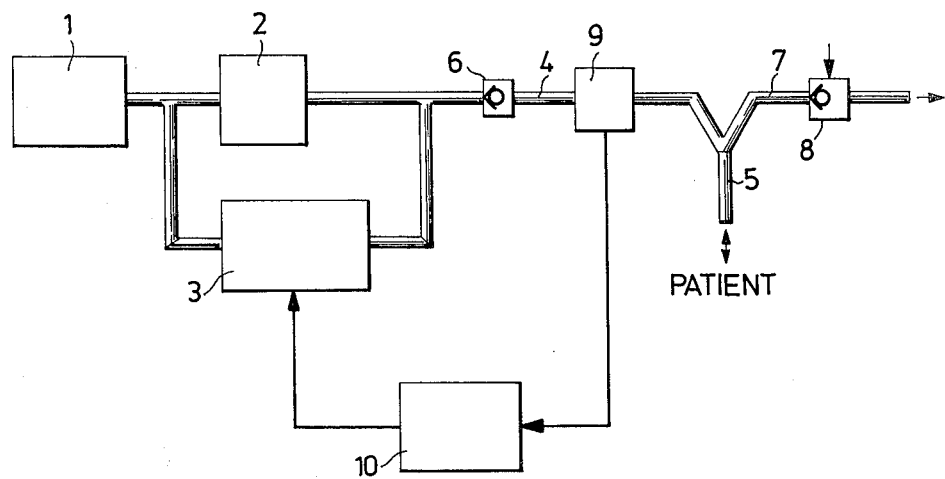

The lung ventilator illustrated very schematically in FIG. 1 comprises, in a conventional manner, a suitable breathing-gas source 1 which is connected to an inspiratory line 4 via a spontaneous-breathing unit 2 and a ventilator unit 3. The inspiratory line 4 is connected to a patient hose 5 which can be connected to the airways of the patient. The inspiratory line 4 includes a suitable inspiratory valve 6 which enables gas to flow through the line 4 towards the patient in only one direction. Also connected to the patient hose 5 is an expiratory line 7 which includes a suitable expiratory valve 8 which will only allow gas to flow through the line 7 in a direction away from the patient. The expiratory valve 8 is suitably controlled in a manner such that it can only be opened when the patient breathes out. The inspiratory line 4 includes a flow meter 9 of suitable design, for example in the form of a constriction and means for measuring the drop in pressure across said constriction, which generates an electric output signal which represents the momentary value of the gas flow through the inspiratory line 4 and the purpose of which will be explained in more detal hereinafter.

The spontaneous-breathing unit 2 and the ventilator unit 3 may be of any known suitable design which enables the patient to obtain breathing gas from the source 1 by spontaneous breathing through the spontaneous-breathing unit 2 under given desired conditions, for example, a given pressure, and such that the ventilator unit 3 can be activated by means of an electrical control signal, to deliver to the patient a mandatory breath of desired gas volume, i.e. tidal volume, and in a desired manner, for example with respect to the time-function of gas flow and/or gas pressure during the mandatory breath. The spontaneous-breathing unit 2 and the ventilator unit 3 are normally incorporated in a single unit in the lung ventilator. A lung ventilator which can be used in conjunction with the present invention is described, for example, in the Swedish Patent Application No.

7905509-1, to which reference is made herewith. This lung ventilator enables a patient connected thereto breathe spontaneously at, for example, a desired adjustable continuous positive airway pressure, CPAP, and can also be activated to deliver to the patient a mandatory breath with a desired, variable tidal volume and a desired, setable time function of flow and/or pressure during the mandatory breath. In the lung ventilator described in the aforementioned patent application the expiratory valve 8 can be controlled in a manner such that the patient exhales against a desired adjustable positive and expiratory pressure, PEEP. Other lung-ventilator designes can also be used in conjunction with the invention, however, provided that they fulfil the aforementioned conditions. When applying the present invention, the breathing-gas source 1 is suitably of such construction that it is able to deliver a quantity of gas corresponding at least to the maximum amount of gas per unit of time which the patient may be expected to require.

For the purpose of carrying out MMV-treatment method, the lung ventilator according to the invention is provided with the flow meter 9 in the inspiratory line 4 and a control unit 10, which receives the measuring signal obtained from the flow meter 9 and corresponding to the momentary value of the flow of breathing gas flowing through the inspiratory line 4, and which activates the ventilator unit 3 by means of an electric control signal to deliver a mandatory breath to the patient.

Figure 2:
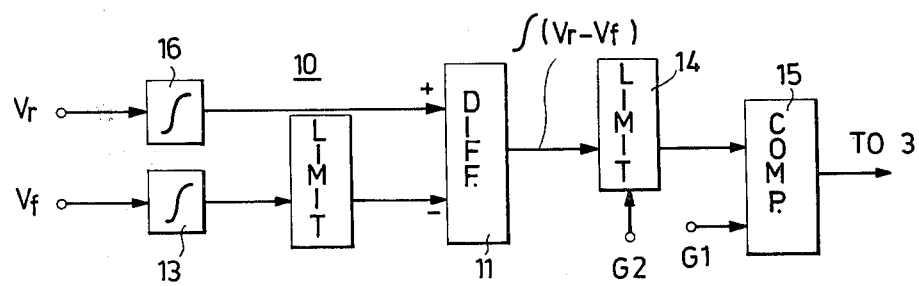
FIG. 2 is a more detailed block diagram of the control unit according to the invention incorporated in the lung ventilator according to FIG. 1.

FIG. 2 illustrates the principle construction of the control unit 10. The control unit 10 receives the flow signal $V_f$ from the flow meter 9 and also a reference or setpoint value signal $V_r$, which is assumed to have the same sign as the flow signal $V_f$ and which for the sake of simplicity can initially be assumed to be constant but the value of which is adjustable. The reference signal $V_r$ and the flow signal $V_f$ are each supplied to an integrating circuit 13 and 16, respectively, which continuously integrate the input signals. The integrated reference signal $\int V_r$ is applied to one input of a subtracking circuit 11, to the other input of which there is applied the integrated flow signal $\int V_f$ via a limiter or threshold circuit 12, the function and purpose of which will be described in more detail hereinafter. The integrated signal $\int V_f$ is subtracted in the circuit 11 from the integrated reference signal $\int V_r$, and hence, if the limiter 12 is considered not to have come into operation or has not been included in the system, the signal $\int(V_r-V_f)$ is produced on the output of the circuit 11. As will be understood, if the limiter 12 is omitted, the subtracting circuit 11 and the integrating circuits 13 and 16 may alternatively be replaced with a single subtracting integrating circuit, or the two signals $V_r$ and $V_f$ may, instead, be first subtracted from one another, whereafter the difference signal is continuously integrated. In all cases the resulting output signal $\int(V_r-V_f)$ will be the same. This signal is applied to a limiting circuit 14, which prevents the signal from falling beneath a pre-determined lower limit value G2, this limit value suitably being adjustable. The output signal from the limiting circuit 14, said signal being identical to the signal $\int(V_r-V_f)$ provided that the limiting circuit 14 does not come into operation, is applied to one input of a comparison circuit 15, while an upper, preferably adjustable, limit value signal G1, which is higher than the previously mentioned limit value G2, is applied to the other input of the comparison circuit 15.

For the purpose of describing the function of the control unit 10 it will be assumed initially, for the sake of simplicity, that the limiting circuit 12 has been omitted and that the limiting circuit 14 has also been omitted or needs never come into operation. Further, it is assumed that the comparison circuit 15 is arranged to deliver an output signal to the ventilator unit 3 when its two input signals $\int(V_r-V_f)$ and G1 coincide. It is also assumed that the reference signal $V_r$ is set to a value corresponding to a flow of breathing gas which equals that minute volume which the patient should at least receive. Finally, it is assumed that the value of the flow signal $V_f$ is zero when no gas flows through the inspiratory line 4.

Figure 3:
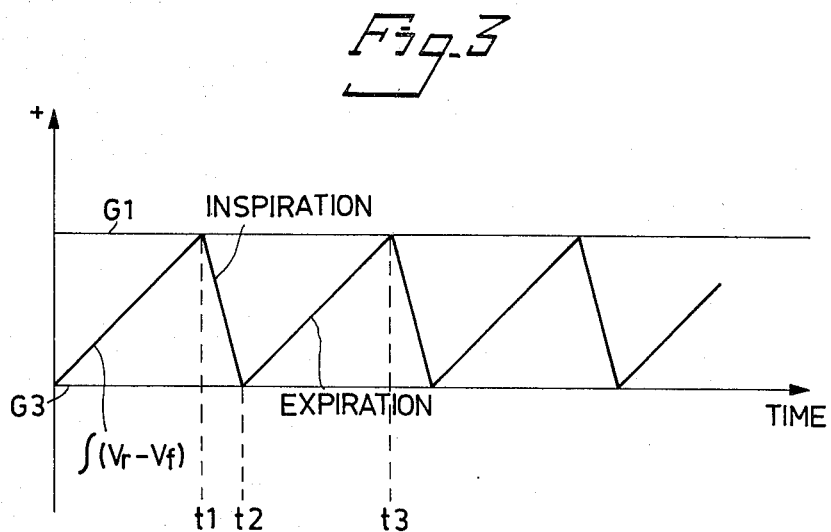
FIG. 3 is a curve illustrating the mode in which the lung ventilator operates when the patient does not breathe spontaneously at all.

With the aforementioned assumptions, the lung ventilator will operate in the manner illustrated by the curve in FIG. 3, when the patient does not breathe spontaneously at all. In this case, the flow signal $V_f$ is zero at the commencement of the respiratory treatment, since the patient makes no attempt to breathe. Consequently, the integrated signal $\int(V_r-V_f)$ is equal to $\int V_r$ and initially rises linearly, as illustrated in FIG. 3. When this integrated signal value reaches the limit value G1 at the time point t1 in FIG. 3, the comparison circuit 15 sends a signal to the ventilator unit 3 which, under the influence of this signal, is activated to deliver to the patient a mandatory breath of pre-determined volume, the tidal volume. Thus, during this mandatory breath the integrated signal $\int(V_r-V_f)$ again falls to a level G3 as shown at the time point t2 in FIG. 3. Thus, the level difference between G1 and G3 corresponds to the integral from t1 to t2 of $(V_r-V_f)$ or, which is the same thing in the present case, the integral from 0 to t1 of the reference signal $V_r$. Thus, a mandatory breath is delivered to the patient between the time points t1 and t2. The patient thereafter breathes out through the expiratory line 7, and the integtrated signal $\int(V_r-V_f)$ again rises linearly to again reach the limit value G1 at the time point t3 in FIG. 3. The patient thus exhales between the time points t2 and t3. At time point t3 the comparison circuit 15 again sends an output signal to the ventilator unit 3, which under the influence of this signal again delivers a mandatory breath to the patient in the manner aforedescribed. This is repeated periodically, provided that the patient makes no attempt to breathe spontaneously. Thus, treatment of the patient corresponds to a controlled mechanical ventilation with a minute volume corresponding to the pre-set value of the reference signal $V_r$ and a pre-set tidal volume. The breathing frequency automatically becomes equal to the ratio of the minute volume $V_r$ and the pre-set tidal volume.

Figure 4:
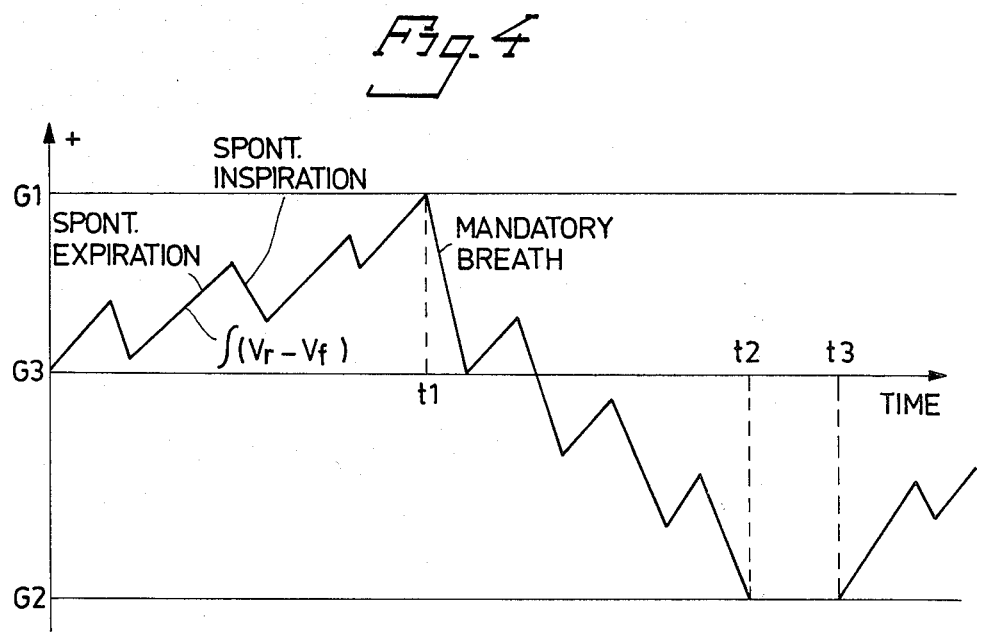
FIG. 4 is a corresponding curve illustrating the mode in which the lung ventilator operates when the patient breathes spontaneously.

If the patient is able to breathe spontaneously, however, the lung ventilator will operate in the manner illustrated, by way of example by the curve shown in FIG. 4. In this case, the integrated signal $\int(V_r-V_f)$ will vary in pace with the patient's spontaneous breathing, as illustrated in FIG. 4, i.e. the value of the signal will fall during the spontaneous inspirations of the patient in dependence upon the amount of gas spontaneously inspired by the paitent, and will rise during the spontaneous expirations of the patient, when $V_f=0$. If the spontaneous breathing of the patient does not, on average, reach the minute volume corresponding to the preset value of the reference signal $V_r$, the integrated signal $\int(V_r-V_f)$, however, will gradually grow up to and reach the limit value G1, as shown at the t1 in FIG. 4. When this occurs the comparison circuit 15 sends, in the manner before described, a signal to the ventilator unit 3 which, under the influence of this signal, delivers to the patient a mandatory breath of said preset tidal volume, whereby the value of the integrated signal $\int(V_r-V_f)$ drops to the level G3, as shown in FIG. 4. The patient can then continue to breathe spontaneously, to the extent to which he is able. If the patient should still inspire less gas than that which, on average, corresponds to the reference value $V_r$, the integrated signal will again gradually climb to the limit value G1, whereupon a further mandatory breath is delivered to the patient. Thus, it is ensured that the patient achieves a total ventilation, by spontaneous breathing and mandatory breaths, at least corresponding to the preset reference value $V_r$.

As beforementioned, the breathing-gas source 1 is suitably so constructed that it is able to supply to the patient, when the patient breathes spontaneously, an amount of gas which exceeds the minute volume corresponding to the preset value of $V_r$ and which at least equals the maximum amount of gas which the patient can conceivably require.

During spontaneous breathing the patient can therefore breathe a larger amount of gas than that corresponding to the reference value $V_r$. Under these conditions, the integrated signal $\int(V_r-V_f)$ will fall to a level beneath the value G3, as illustrated to the right in FIG. 4, and will continue to fall as long as the patient breathes spontaneously in the said manner. In this way it is possible for the integrated signal to fall to a very low value, and should the patient subsequently, for some reason or other, suddenly cease to breathe spontaneously, it might take a very long time before the integrated signal reaches the limit value G1 and a mandatory breath is delivered to the patient. This drawback can be eliminated in accordance with the invention, however, by passing the signal $\int(V_r-V_f)$ through the limiter circuit 14, which is designed to limit the integrated signal and prevent it from falling beneath a signal value G2, as shown in FIG. 4. The limit value G2 must be selected to lie beneath the value G3. When the integrated signal reaches the lower value G2, as a result of vigorous spontaneous breathing by the patient, which is illustrated in FIG. 4 to occur at time point t2, the integrated signal is limited to the value G2, and is clamped at said value, until said vigorous spontaneous breathing by the patient ceases and the signal difference $(V_r-V_f)$ again becomes positive, such that the integrated signal $\int(V_r-V_f)$ again begins to rise, which in the FIG. 4 example takes place at the time point t3.

Thus, the invention enables a patient to breathe spontaneously more vigorously than that corresponding to the preset minute volume $V_r$, without any risk to the patient, even if the patient should suddenly cease to breathe spontaneously after such a period of vigorous spontaneous breathing.

The problem of panting of the patient, i.e. shallow and rapid breathing, mentioned in the introduction and encountered with previously known lung ventilator constructions for MMV-treatment, can be eliminated in accordance with the invention with the aid of the threshold or limiting circuit 12. The circuit 12 is so designed that of the incremented increases in the value of the integrated flow signal $\int V_f$ occurring with each inhalation by the patient, either spontaneous or mandatory, and corresponding to the gas volume of each inhalation the circuit 12 will only pass on those incremental increases having a value exceeding a given minimum value, i.e. a given minimum volume of breathing gas with each inhalation. In this way the control unit 10 will not take notice of those inhalations of small volume which occur when the patient pants and which do not have any actual effect on the ventilation of the patient. In this way the patient is ensured satisfactory ventilation, even if he or she should pant.

In the aforedescribed embodiment of the invention the control unit 10 controls the frequency of mandatory breaths delivered to the patient by means of the ventilator unit 3, while the tidal volume for each said mandatory breath is determined and present in the ventilator unit 3. It is conceivable, however, to use another embodiment of the invention, in which the ventilator unit 3 is preset and arranged to deliver to the patient mandatory breaths at a pre-determined frequency, while the control 10 causes the ventilator unit 3 to adapt the tidal volume of these mandatory breaths in dependence on the magnitude of the difference between the limit value G1 and the integrated signal $\int(V_r-V_f)$ at the time point when such a mandatory breath shall be delivered. Thus, the comparison circuit 15 detects this difference and sends a corresponding control signal to the ventilator unit 3. Thus, in this case the control unit 10 controls the tidal volume of the mandatory breaths, while the frequency of said breaths is preset.

In the aforegoing it has been assumed that the reference signal $V_r$ is preset to a value which corresponds with that minute volume of breathing gas which the patient should at least receive. It is also possible, however, to adjust or vary this reference signal $V_r$ in dependence on other physiological parameters, such as the desired alveolar ventilation of the patient.

In the aforedescribed embodiment of the invention the flow of gas through the inspiratory line 4 is measured by means of the flow meter 9. Since, however, when seen in total, the flow of gas through the expiratory line 7 is equal to the flow of gas through the inspiratory line 4, it is also possible in accordance with the invention to incorporate the flow meter 9 in the expiratory line 7 in order to measure the flow of gas therethrough.

We claim:

1. A method of controlling operation of a lung ventilator, which includes a source of breathing gas having means capable of delivering a volume of breathing gas per unit of time; which is at least equal to the maximum volume that may be required for the ventilation of the patient, an inspiratory line having means for connecting the same to the airways of a patient and through which the patient can breathe spontaneously from said breathing-gas source, a ventilator unit connected to said breathing-gas source and activateable by an activation signal to deliver to the patient through said inspiratory line a mandatory breath of a predetermined tidal volume from said breathing-gas source, and an expiratory line having means for connecting the same to the airways to the patient and through which the patient can exhale, the method comprising the steps of sensing continuously the flow rate of breathing gas through said inspiratory line and generating a signal proportional to the momentary value of said flow rate, producing a reference signal substantially proportional to the minimum volume per unit of time, the so called minute volume, of breathing gas which the patient shall receive, said minimum volume per unit of time being less than the volume that the breathing gas source is capable of delivering, calculating continuously the total integral, during the entire inhalation and exhalation cycles of ventilation of the patient, of the difference between said reference signal and said flow rate signal and generating continuously a signal proportional to said integral, producing a first threshold signal substantially proportional to said tidal volume of a mandatory breath, comparing continuously said signal proportional to said integral and said first threshold signal, and producing an activation signal for activating said ventilator unit to deliver a mandatory breath of said predetermined tidal volume to the patient each time the value of said signal proportional to said integral reaches the value of said first threshold signal.

2. A method as claimed in claim 1, comprising the additional steps of providing a second threshold value lower than the value of said first threshold signal and selected to be lower than the value of said signal proportional to said integral at the end of a mandatory breath delivered to the patient by said ventilator unit, and limiting said signal proportional to said integral downwardly so as to prevent its value from falling beneath said second threshold value.

3. A method as claimed in claim 1, wherein the value of said reference signal is varied to correspond to an average volume per unit of time of breathing gas which, when delivered to the patient, produces a desired alveolar ventilation of the patient.

4. A method as claimed in claim 1, wherein said integral is calculated by determining continuously the total integral of said flow rate signal and also determining continuously the total integral of said reference signal, subjecting the integral of the flow rate signal to a limitation eliminating any incremental increasings in said integral which are smaller than a given minimum value, and subtracting this limited integral of the flow rate signal from said integral of the reference signal.

5. A device for controlling the operation of a lung ventilator including a breathing-gas source having means capable of delivering a volume of breathing gas per unit of time, which is at least equal to the maximum volume that may be required for the ventilation of the patient, an inspiratory line having means for connecting the same to the airways of a patient and through which the patient can breathe spontaneously from said breathing-gas source, a ventilator unit connected to said breathing-gas source and activatably by an activation signal to deliver to the patient through said inspiratory line a mandatory breath of a predetermined tidal volume from said breathing-gas source, and an expiratory line having means for connecting the same to the airways of the patient and through which the patient can exhale, said device comprising a flow meter for sensing continuously the flow rate of breathing gas through said inspiratory line and generating a signal proportional to the momentary value of said flow rate, means for producing a reference signal substantially proportional to the minimum volume per unit of time, the so called minute volume, of breathing gas which the patient shall receive, said minimum volume per unit of time being less than the volume that the breathing gas source is capable of delivering, means for calculating continuously the total integral, during the entire inhalation and exhalation cycles of ventilation of the patient, of the difference between said reference signal and said flow rate signal and for producing a signal proportional to this integral, means for providing a first threshold signal having a value substantially proportional to said predetermined tidal volume of a mandatory breath, and means for comparing the value of said signal proportional to said integral and said first threshold signal and generating an activation signal for activating said ventilator unit to deliver a mandatory breath to the patient each time the value of said signal proportional to said integral reaches the value of said first threshold signal.

6. A device as claimed in claim 5, wherein said means for calculating said integral include means for determining continuously the total integral of said reference signal, means for determining continuously the total integral of said flow rate signal, means for limiting the last mentioned integral to eliminate therefrom any incremental increases in the integral which fall below a given minimum value, and means for subtracting said limited integral of the flow rate signal from said integral of said reference signal.

7. A device as claimed in claim 5, comprising means for providing a second threshold signal having a value lower than said first threshold signal and also lower than the value of said signal proportional to said integral at the end of a mandatory breath, and a limiting circuit for limiting the value of said signal proportional to said integral so as not to fall beneath the value of said second threshold signal.

8. A method of controlling the operation of a lung ventilator, which includes a source of breathing gas, having means capable of delivering a volume of breathing gas per unit of time, which is at least equal to the maximum volume that may be required for the ventilation of the patient, an inspiratory line having means for connecting the same to the airways of a patient and through which the patient can breath spontaneously from said breathing-gas source, a ventilator unit connected to said breathing-gas source for delivering to the patient through said inspiratory line with a predetermined frequency mandatory breaths of a variable tidal volume determined by the magnitude of a control signal supplied to the ventilator unit, and an expiratory line having means for connecting the same to the airways of the patient and through which the patient can exhale, the method comprising the steps of sensing continuously the flow rate of breathing gas through the inspiratory line and producing a signal proportional to the momentary value of this flow rate, producing a reference signal substantially proportional to the minimum volume per unit of time, the so called minute volume, of breathing gas which the patient shall receive, said minimum volume per unit of time being less than the volume that the breathing gas source is capable of delivering, calculating continuously the total integral, during the entire inhalation and exhalation cycles of ventilation of the patient, of the difference between said reference signal and said flow rate signal and producing a signal proportional to this integral, producing a threshold signal having a value corresponding to a largest acceptable deficit in volume of breathing gas received by the patient from the beginning of the ventilation of the patient.

comparing said signal proportional to said integral with said threshold signal at the time of each mandatory breath delivered by said ventilator unit to the patient and producing a control signal to the ventilator unit for determining the tidal volume of said mandatory breath dependent on the difference between the signal proportional to said integral and said threshold signal.

9. A device for controlling the operation of a lung ventilator including a breathing-gas source having means capable of delivering a volume of breathing gas per unit of time; which is at least equal to the maximum volume that may be required for the ventilation of the patient, an inspiratory line having means for connecting the same to the airways of a patient and through which the patient can breath spontaneously from said breathing-gas source, a ventilator unit connected to said breathing-gas source for delivering to the patient through said inspiratory line with a predetermined frequency mandatory breaths of a variable tidal volume determined by the magnitude of a control signal supplied to the ventilator unit, and an expiratory line having means for connecting the same to the airways of the patient and through which the patient can exhale, said device comprising a flow meter for continuously sensing the flow rate of breathing gas through the inspiratory line and generating a signal proportional to the momentary value of this flow rate, means for generating a reference signal substantially proportional to the minimum volume per unit of time, the so called minute volume, of breathing gas which the patient shall receive, said minimum volume per unit of time being less than the volume that the breathing gas source is capable of delivering, means for calculating continuously the total integral, during the entire inhalation and exhalation cycles of ventilation of the patient, of the difference between said reference signal and said flow rate signal and for producing a signal proportional to this integral, means for producing a threshold signal having a value corresponding to a largest acceptable deficit in volume of breathing gas received by the patient from the beginning of the ventilation of the patient, and means for comparing said signal proportional to said integral with said threshold signal and for producing a control signal to said ventilator unit for determining the tidal volume of each mandatory breath in dependence of the difference prevailing at the time of each mandatory breath between the value of said signal proportional to said integral and the value of said threshold signal.

* * * * *